United States Patent [19]
Jackson

[11] 4,134,732
[45] Jan. 16, 1979

[54] FLOATING METHANOL PLANT

[75] Inventor: Robert G. Jackson, Ponca City, Okla.

[73] Assignee: Continental Oil Company, Ponca City, Okla.

[21] Appl. No.: 804,650

[22] Filed: Jun. 8, 1977

[51] Int. Cl.² .................. B01D 3/00; B63B 35/28; C07C 29/16

[52] U.S. Cl. .................... 422/198; 23/263; 114/26; 114/264; 203/DIG. 16; 210/242 R; 260/449.5; 422/211

[58] Field of Search .................. 23/260, 262, 263; 48/196 A, 196 R, 196 U, 196 S; 210/242 R; 114/26, 264, 270; 260/449.5; 203/DIG. 16

[56] References Cited

U.S. PATENT DOCUMENTS

| | | | |
|---|---|---|---|
| 1,833,717 | 11/1931 | Laird | 23/263 UX |
| 2,382,944 | 8/1945 | Porter | 23/263 X |
| 2,541,657 | 2/1951 | Lynch et al. | 48/196 A |
| 2,703,788 | 3/1955 | Morrisroe | 23/260 X |
| 2,749,212 | 6/1956 | Crowder | 23/262 X |
| 2,813,900 | 11/1957 | Dunlop et al. | 23/260 X |
| 3,262,411 | 7/1966 | Kaltenecker | 114/26 |
| 3,404,957 | 10/1968 | Blaskowski | 23/260 X |

OTHER PUBLICATIONS

Chemical Week, vol. 119, No. 21, pp. 70-71 (Nov. 24, 1976).

Primary Examiner—Joseph Scovronek
Attorney, Agent, or Firm—Richard W. Collins

[57] ABSTRACT

Methanol is produced from offshore natural gas in a plant positioned on a floating structure. The plant incorporates heat recovery equipment and storage facilities providing the flexibility to operate portions of the plant independently so that motion-sensitive parts of the plant, such as tall distillation columns for methanol purification, can be operated only during good weather, while sections of the plant less sensitive to motion can operate during more severe weather.

2 Claims, 1 Drawing Figure

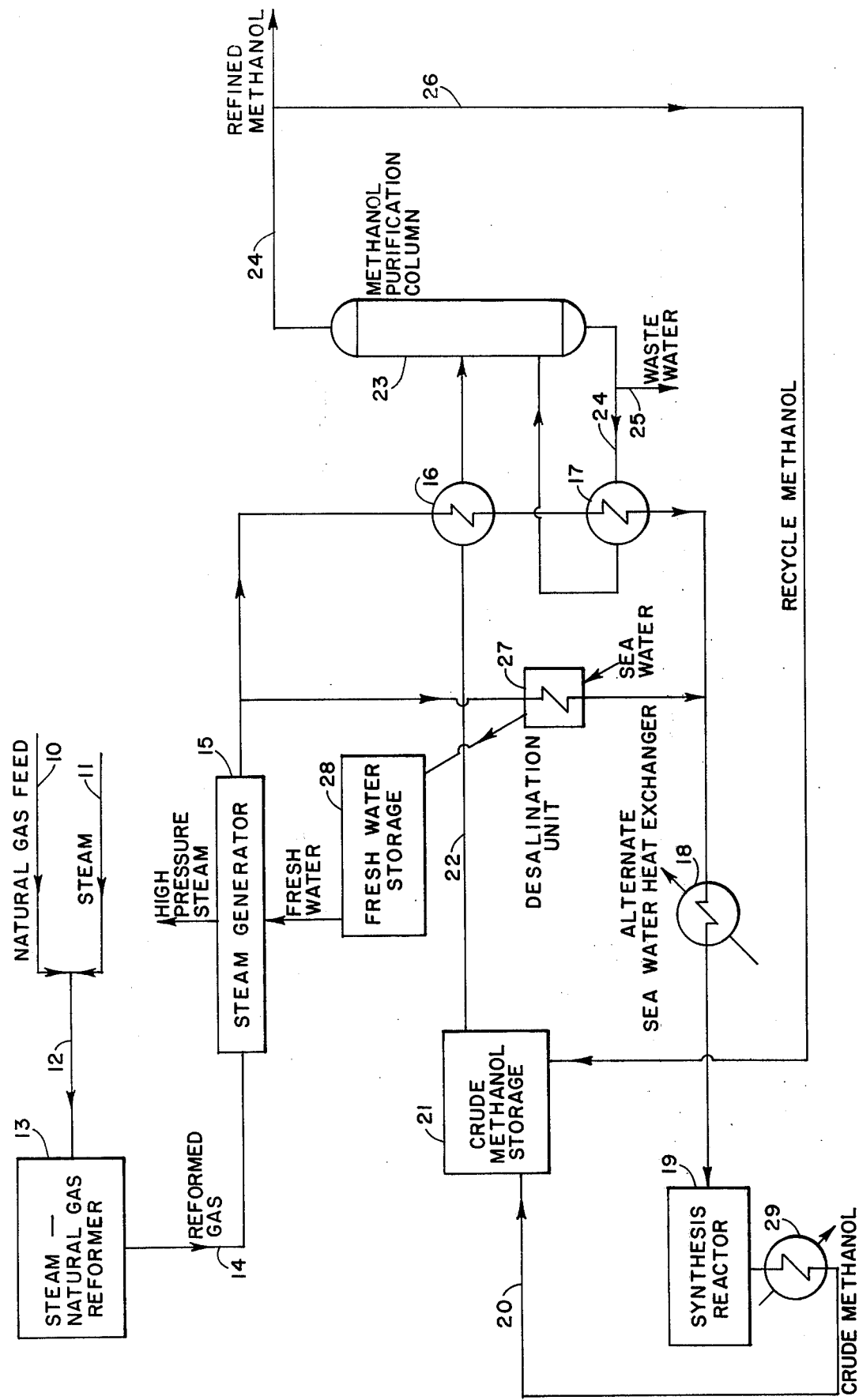

FLOATING METHANOL PLANT

BACKGROUND OF THE INVENTION

1. Field of the Invention

This invention relates to the production of methanol from offshore natural gas by processing the natural gas in a plant erected on a floating structure.

Crude oil exploration is taking place throughout the world in offshore areas, and in many cases gas is found associated with oil but in quantities too small to be economically transported to shore. This gas must therefore either be wastefully burned or returned to the formation at considerable expense.

Several approaches have been suggested for utilizing offshore gas where it occurs in amounts unsuitable for pipelining to shore. One such method involves liquefaction of the natural gas followed by transportation of the liquefied natural gas to an onshore processing facility. This approach is attractive in some respects, but is subject to considerable economic and processing limitations. Another approach which has been suggested is to produce ammonia or urea on a floating structure. The other alternative which has been considered by the industry is construction of a floating methanol plant for use at offshore gas sites.

2. Prior Art

As mentioned above, the broad idea of constructing a processing plant on a floating structure for use at an offshore gas site is well known. A general discussion of the alternatives and the advantages and disadvantages of various approaches appears in the Nov. 24, 1976 issue of *Chemical Week*. As noted in that article, the problems involved are of such a magnitude that there are no existing facilities for processing natural gas on a floating structure.

An ice plant constructed on a ship is described in U.S. Pat. No. 2,630,091, and U.S. Pat. No. 3,837,308 describes a floating power plant.

Plants for the production of methanol using natural gas as a feedstock are well known. These plants consist of a feed gas pre-treatment plant, a steam-natural gas reformer, a steam-producing waste heat recovery system usually combined with the exhaust of the reformer, a synthesis reactor and a distillation section. In these plants, a large amount of heat is produced in the synthesis reactor, and unless a large portion of this heat is recovered, then the process will be very inefficient. Many recent methanol plants utilize a basic design developed by Imperial Chemicals Industries and known generally as the ICI low-pressure methanol process. This process is described in the January 1975 issue of *Hydrocarbon Processing*. The *Hydrocarbon Processing* article also describes variations in which the heat for the reboiler of the distillation columns is obtained from the reformed gas as an energy conservation measure. Plants utilizing the ICI design are presently available, and the basic process of converting natural gas to methanol does not constitute a part of this invention.

A processing plant located on a floating structure is subject to motion from wave action and weather conditions, and certain types of process equipment are more sensitive to motion than others. In particular, tall distillation columns are extremely sensitive to motion, as the efficiency of the columns drops drastically if the columns deviate more than a very few degrees from the vertical, and desalination units which are necessary for production of fresh process water when the plant is located in sea water are sensitive to motion, and must be designed somewhat oversize and fresh water storage means provided to allow the plant to operate using stored fresh water during severe weather. On the other hand, the other sections of a methanol plant using natural gas as a feedstock are not particularly sensitive to motion, and can be operated more or less normally even in reasonably severe weather conditions on a floating structure. Accordingly, a conventional methanol plant cannot be effectively used on a floating structure because of the sensitivity of the distillation section and desalination unit to motion, and modifications are necessary in order to provide an efficient plant on a floating structure.

It is an object of the present invention to provide an efficient and flexible plant for the production of methanol from offshore natural gas on a floating platform.

It is a further object to provide such a plant wherein the distillation section and desalination unit are independent of the rest of the plant such that they can be shut down during severe weather without the necessity for shutting down the entire plant.

SUMMARY OF THE INVENTION

According to the present invention, a plant for making methanol from natural gas feed is erected on a floating structure such as a barge.

The methanol plant in accordance with the invention differs from a conventional methanol plant in that storage means are provided between the methanol synthesis reactor and the methanol distillation unit and between the desalination unit and the boiler so that the synthesis reactor can continue to produce crude methanol over a period of time during which the distillation unit and desalination unit are shut down or ineffective due to excessive motion of the floating structure caused by weather or wave action. Additionally, an alternate heat exchanger is provided to remove heat from the synthesis gas stream which would normally be removed in the distillation and desalination units. This alternate heat exchanger preferably utilizes sea water as a cooling medium. The desalination unit, as will be apparent, will only be needed when the plant is operating in sea water.

BRIEF DESCRIPTION OF THE DRAWINGS

The FIGURE is a schematic flow sheet illustrating a methanol plant in accordance with the invention.

DESCRIPTION OF THE PREFERRED EMBODIMENT

The ability of a methanol plant to operate on a floating structure depends on the stability of the floating structure, and particularly on its pitch and roll characteristics. This invention provides a system of heat recovery which enables different parts of the plant to run independently of each other so that the units particularly sensitive to motion need only be operated when the structure is not being subjected to forces which produce sufficient motion to make the motion-sensitive units inefficient.

The reaction to form synthesis gas from methane and steam is $CH_4 + H_2O \rightarrow CO + 3H_2$, and in order to force this reaction to approach equilibrium in a reformer a considerable excess of steam must be used. Thus, before the synthesis gas can be passed to the synthesis reactor, the excess steam must be removed from the synthesis gas by cooling and condensation.

This can be done by the production of steam for the power and process systems.

The synthesis reactions to produce methanol are $CO + 2H_2 \rightarrow CH_3OH$ and $CO_2 + 3H_2 \rightarrow CH_3OH + H_2O$, and to obtain optimum efficiency in hydrogen utilization it is preferred to combine these two reactions in a single synthesis reactor. The product from the synthesis reactor consists of methyl alcohol and water together with unreacted synthesis gases and traces of higher alcohols and ethers.

About one mol of fresh water must be provided for each mol of methanol produced, and there is accordingly a continuous requirement, while the plant is operating, for fresh process water which must be produced from sea water when the methanol plant is located in offshore ocean water. This fresh process water can be produced with a desalination unit using heat from the reformer gas stream to distill fresh water from sea water, and a reserve can be accumulated during good weather for use during bad weather when the desalination unit is ineffective.

The stream of gas emanating from the reformer tubes can be cooled by direct heat exchange with water so that the water is converted to high pressure steam. This stream can also be used to provide the heat requirements of a sea water desalination unit, a boiler feed water de-aerater, and a crude methanol distillation unit. The stream is finally cooled by heat exchange with sea water, and the piping of the stream is such that any or all of the process equipment can be bypassed so that the main part of the plant can continue to operate while parts sensitive to sea motion, such as the distillation unit, can be shut down.

Storage for crude methanol from the synthesis reactor must be provided between the synthesis reactor and the distillation unit to accumulate crude methanol product while the distillation unit is shut down. Basically, the invention provides a process plant for the production of fuel grade methanol comprising a conventional gas pretreatment section, a steam methane reformer, a compression section, a methanol synthesis reactor, and a distillation unit. Additionally, piping, controls and storage are arranged to permit intermittent operation of the rest of the plant when motion of the floating structure necessitates shut-down of the distillation and/or desalination units or when motion of the structure causes the efficiency of the distillation and/or desalination units to drop.

The details of the basic methanol plant will not be discussed at length, as they are conventional. Those skilled in the art will recognize that extensive piping, controls, gas and liquid handling systems, heat exchangers and instrumentation in excess of that illustrated in the drawing are required for a plant of the type to which this invention is directed.

The preferred embodiment of the invention will now be described with reference to the drawing. Natural gas feed from line 10 and internally produced process steam from line 11 are combined in line 12 and fed to a steam-natural gas reformer 13 where the methane and steam react to produce primarily carbon monoxide and hydrogen with some carbon dioxide. This synthesis gas from reformer 13 which includes a large amount of heat and excess steam passes from line 14 through steam generator 15. The synthesis gas stream then passes through heat exchangers 16, 17 and 18, the functions of which will be described in detail below. A portion of the stream is utilized in desalination unit 27 to evaporate sea water and produce fresh process water. After passing through the steam generator and the series of heat exchangers, the reformed gas stream is fed to synthesis reactor 19 where the carbon oxides react with hydrogen to produce a crude methanol product. The crude methanol product from reactor 19 passes via line 20 to a crude methanol storage tank 21 after cooling and condensation in heat exchanger 29. It will be appreciated that a series of condensers, compressors, and related process equipment are provided in the reformed gas line and the crude methanol product line to condense steam from the reformed gas, to separate gases from the crude methanol product and to recover energy from the streams in accordance with good engineering practice.

The crude methanol from storage tank 21 passes through line 22 and is heated in heat exchanger 16 before being fed to methanol purification column 23. Refined methanol suitable for use as a fuel is recovered through line 24 and either stored on the barge or transferred directly to a tanker or other storage facility for transportation to shore. Most of the heat for the operation of methanol purification column 23 is obtained from heat exchanger 17 which functions as a reboiler for the purification column 23. Bottoms material from the purification column is circulated through line 24 to heat exchanger 17 and returned to the purification column in a conventional manner, and waste water is taken off through line 25.

The foregoing describes the process in accordance with the invention during normal operation of the plant in which all of the sections of the methanol plant are functioning normally. This operation is only possible during periods when the floating structure supporting the plant is not producing motion sufficient to interfere with the operation of the methanol purification and sea water desalination units. Depending on the feed rate to the purification column 23 and the excess capacity designed therein, the purification column can only produce an adequately refined product when the floating structure is moving through a rather small angle of pitch and/or roll. The efficiency of a distillation column drops rapidly with increasing angle, and a pitch or roll of about 3 degrees generally is the maximum that can be tolerated. Also, the desalination unit 27 becomes inefficient under these conditions such that process water must be obtained from fresh water storage means 28 under such conditions. Desalination unit 27 has sufficient capacity to provide an excess of fresh water over the amount needed for plant operation, and the excess is stored in storage means 28 for use when the desalination unit is shut down.

The operation of the plant when weather conditions or other factors cause excess motion, such as greater than a 3 degree roll, will now be described.

Normally, during adverse weather conditions, the methanol purification and sea water desalination units are completely shut down. The crude methanol feed from storage tank 21 is shut off, as is the desalination unit, and the synthesis gas then passes through heat exchangers 16 and 17 without being cooled therein. In order to recover the heat that would normally be removed in heat exchangers 16 and 17 and desalination unit 27, and to properly condition the synthesis gas stream for feed to the synthesis reactor 19, alternate sea water heat exchanger 18 is activated and the reformed gas cooled therein approximately the same amount as it would normally be cooled in heat exchangers 16 and 17 and desalination unit 27. It will be appreciated that heat exchanger 18 is preferably not utilized when the distillation and desalination units are operating, although it may be used to a lesser extent if desirable. In the mode where the purification and desalination units are not operating, crude methanol from the synthesis reactor is accumulated in storage tank 21 and fresh water is taken from storage tank 28 until such time as the units are again activated.

The capacity of storage tanks 21 and 28 is preferably designed to handle the plant production for a period of three days or more. Weather records for the particular location of the plant can provide a good indication of the frequency and duration of adverse weather periods which are likely to be encountered. It is desirable to have additional storage as a safeguard, but the limited space available on a floating plant requires that the storage capacity be no more than is expected to be needed.

There will occasionally be borderline conditions during which it is not desirable to shut down the distillation column but in which the motion is such that the column does not produce a satisfactorily refined product. In this situation, inadequately refined methanol can be recycled through line 26 back to methanol storage tank 21 and subsequently redistilled.

Specific process equipment sizes and capacities do not constitute a part of this invention, as they are readily determined. For example, a plant capable of manufacturing about 2,000 tons per day of methanol can be purchased as a unit. The modifications required in accordance with this invention can be made at the time that the basic plant is installed on a floating structure. The particular size of the plant depends on the volume of natural gas feed available at a particular location and upon the availability of plants of a particular size as well as on economic considerations and market conditions for the product methanol.

Summarizing, the features in accordance with this invention which enable a methanol plant to be operated on a floating structure include the provision of an alternate sea water heat exchanger to absorb the heat from the synthesis gas stream in the event that the methanol purification and sea water desalination units are inactivated. Additionally, crude methanol storage means must be provided, and preferably means are included to recycle distilled methanol back to crude methanol storage to allow for conditions in which the distilled methanol does not meet product specifications.

It will be appreciated that a methanol plant located on a floating structure could be used in a body of fresh water, in which case the desalination unit would not be necessary. However, most situations in which a natural gas feed is available a considerable distance from shore are, and will be in the future, in association with ocean water rather than fresh water.

The foregoing detailed description of the most preferred embodiment of the invention is intended to be illustrative rather than limiting of the invention, and numerous variations and modifications will be apparent to those skilled in the art which are within the true scope of the invention, which is to be defined by the appended claims.

I claim:

1. In a plant for producing methanol from natural gas, said plant being mounted on a floating structure and comprised of a steam-natural gas reformer, a synthesis reactor and a distillation unit for purification of methanol produced in the synthesis reactor and wherein steam-containing gas from the reformer provides heat for the distillation unit, the improvement comprising:

a desalination unit for making fresh water for said plant from sea water, said desalination plant utilizing heat from reformed gas produced in said reformer;

fresh water storage means for storing desalinated water produced in said desalination unit, said fresh water storage means having a capacity sufficient to store enough desalinated water to operate said plant for at least three days;

heat exchanger means between said reformer and said synthesis reactor for reboiling bottoms from said distillation unit, said heat exchanger means being adapted to exchange heat between said reformed gas and the bottoms from said distillation unit;

alternate heat exchanger means between said reformer and said synthesis reactor for conditioning reformed gas ahead of said synthesis reactor, said alternate heat exchanger being cooled by water from the body in which said floating structure is floating and having sufficient capacity to condition reformed gas going to said synthesis reactor when said desalination unit and said distillation unit are not being operated;

crude methanol storage means between said synthesis reactor and said distillation unit, said crude methanol storage means having a capacity of at least three days of crude methanol production; and means for selectively shutting down said desalination unit and said distillation unit during adverse weather while said reformer and synthesis reactor continue to operate.

2. A plant according to claim 1 including piping means for returning product from the distillation unit directly back to the crude methanol storage means.

* * * * *